(12) United States Patent
Ishiyama et al.

(10) Patent No.: US 7,395,107 B2
(45) Date of Patent: Jul. 1, 2008

(54) MAGNETOCARDIOGRAPH

(75) Inventors: Atsushi Ishiyama, Tokyo (JP); Yumie Ono, Tokyo (JP); Masahiro Murakami, Hitachinaka (JP)

(73) Assignees: Waseda University, Tokyo (JP); Hitachi High-Technologies Corporation, Tokyo (JP)

( * ) Notice: Subject to any disclaimer, the term of this patent is extended or adjusted under 35 U.S.C. 154(b) by 507 days.

(21) Appl. No.: 11/042,202

(22) Filed: Jan. 26, 2005

(65) Prior Publication Data

US 2005/0192502 A1   Sep. 1, 2005

(30) Foreign Application Priority Data

Feb. 27, 2004   (JP)   ............................. 2004-053973

(51) Int. Cl.
*A61B 5/05*   (2006.01)
(52) U.S. Cl. .................. 600/409; 600/508; 600/523
(58) Field of Classification Search ............... 600/409, 600/508, 512
See application file for complete search history.

(56) References Cited

U.S. PATENT DOCUMENTS 5,206,589 A * 4/1993 Kado et al. ............... 324/248
6,187,032 B1 * 2/2001 Ohyu et al. ............... 600/409
2003/0149354 A1 * 8/2003 Bakharev .................. 600/407

* cited by examiner

*Primary Examiner*—Carl H. Layno
*Assistant Examiner*—Eugene T Wu
(74) *Attorney, Agent, or Firm*—Dickstein Shapiro LLP

(57) ABSTRACT

In magnetocardiography, an assisting technique for a doctor diagnosing a heart disease will be provided. In the magnetocardiography, magnetism to be generated from a subject's heart is measured by a magnetic sensor, and from this measured data, a position of center of gravity of excitement wave front in a cardiac muscle excitement propagation process and a transition vector (wave front vector) is calculated by an analyzing computer. With this wave front vector as a feature parameter, the Mahalanobis' distance is calculated from a data base obtained by diagnosing in the past, a possibility (probability) of the subject having a heart disease is presumed on the basis of the Bayes' theorem for displaying. Also, by superimposing on a heart picture, the wave front vector position is displayed, and a cluster classification position in the wave front vector is displayed. Also, by the similar retrieval, another subject extremely similar to the subject in the feature parameter will be retrieved from the data base for screen displaying.

12 Claims, 8 Drawing Sheets

MCG MAP (ISOFIELD CONTOUR MAP OF HEART MAGNETIC FIELD)

<CONVENTIONAL ANALYSIS>   <ANALYSIS OF THE PRESENT INVENTION>

MAGNETOCARDIOGRAPH

FIELD OF THE INVENTION

The present invention relates to a magnetocardiograph for measuring a faint magnetic signal to be generated from a heart of man or the like, and more particularly to a diagnosis assisting function for a doctor diagnosing a heart disease.

BACKGROUND OF THE INVENTION

A heart magnetic signal to be generated from a heart of an adult, an infant, an unborn baby and the like is detected using a SQUID (Superconducting Quantum Interference Device) fluxmeter. As a conventional organic magnetic field observation device using this SQUID, there are Patent Documents 1, 2, and 3 or the like. Here, there has been described a device comprising a plurality of fluxmeters for detecting a organic magnetic signal to be generated from an organism including a heart magnetic signal to be generated from the heart, processor means for processing the signal and means for displaying the processor result, for measuring organic magnetism distribution within a magnetic shield room.

Patent Document 1
  Japanese Patent Laid-Open No. 51798/1998

Patent Document 2
  Japanese Patent Laid-Open No. 104098/1999

Patent Document 3
  Japanese Patent Laid-Open No. 104100/1999

The above-described conventional technique relates to a display method for displaying data measured by a measuring device for organic magnetism including heart magnetism so as to make it easier to understand and effectively, and describes a magnetocardiography such as isowaveform display, isofield contour map display and isointegral map display. In order to see these magnetocardiography for diagnosing a heart disease, however, a doctor must obtain high-level knowledge concerning the working principle of the magnetocardiograph and heart disease is required. Further, there have been cases which must rely on subjective experience and judgment of the doctor such as comparing the magnetocardiography data thus obtained with enormous heart disease data concerning magnetocardiography obtained by diagnosing in the past, and judging whether or not that pattern is similar; if similar, to what extent both are similar, and the like. Also, there are various analyzing methods depending upon a disease to be diagnosed, and there have been a problem that it would take a long time when those diseases are diagnosed by analyzing one by one, and the like.

SUMMARY OF THE INVENTION

It is an object of the present invention to provide a magnetocardiograph having a heart disease diagnosis assisting function capable of supporting a doctor's diagnosis without relying on subjective experience and judgment of the doctor in view of the above-described problem of the conventional technique. Also, it is the object to provide a magnetocardiograph leading to the shortened doctor's diagnosis time period because of simple and easy analyzing operation and preventing the doctor from overlooking a disease.

In order to solve the above-described problem, according to the present invention, the magnetocardiograph quantitatively extracts the features from the magnetocardiography data obtained, automatically compares with patterns of data obtained by diagnosing in the past, presumes whether or not it is a heart disease, and presumes candidature for the heart disease.

In other words, a magnetocardiograph for measuring magnetism to be generated from a subject's heart by at least one magnetic sensor comprises: storage means for storing a heart magnetic signal thus measured; calculation means for calculating a position of center of gravity of excitement wave front in a cardiac muscle excitement propagation process and a transition vector (hereinafter, referred to as a wave front vector) from information of the heart magnetic signal stored in the storage means; and display means for displaying an analysis result.

The above-described calculation means prepares an isofield contour map for a heart magnetic field from the heart magnetic signal, calculates the above-described wave front vector on an isofield contour map obtained by spectrum analyzing by means of Wavelet approximation, and projects the calculated wave front vector on the isofield contour map before the Wavelet approximation. In this respect, in place of the Wavelet approximation, Fourier transform or Wavelet transform may be used.

Also, the above-described calculation means regards the wave front vector as a feature parameter, and on the basis of a cluster classification data base of feature parameters obtained by measuring a plurality of previous subjects in advance, classifies cluster patterns of those previous subjects.

Also, the above-described calculation means calculates a Mahalanobis' distance between a center of gravity of each cluster pattern of the cluster classification data base and the feature parameter of the subject, and judges, on the basis of the information of the Mahalanobis' distance obtained, to which cluster pattern the feature parameter of the subject belongs.

Also, the above-described calculation means calculates probability of being a normal person and probability of being a heart disease patient from the judgment result using the cluster pattern on the basis of Bayes' theorem.

Also, the above-described calculation means judges, from the above-described probability of being a normal person and probability of being a heart disease patient, whether the subject is a normal person or a heart disease patient.

Further, the above-described calculation means performs the following display processing. The calculation means judges, from the above-described probability of being a normal person and probability of being a heart disease patient, whether the subject is a normal person or a heart disease patient, for displaying.

The above-described calculation means displays at what probability various heart diseases apply to the subject on the basis of Bayes' theorem.

The above-described calculation means superimposes the above-described wave front vector on a heart image such as a spurious heart picture prepared in advance, or an X-ray CT image, or a MRI image for displaying.

The above-described calculation means selects a plurality of wave front vectors at optional measurement time of the subject, and superimposes a plurality of wave front vectors on an image for displaying.

The above-described calculation means calls data of another subject extremely close (similar) in the Mahalanobis' distance, for displaying. Another subject's data that is said here includes not only the data of the wave front vector, but also image data of magnetocardiography data such as isowaveform and MCG map (isofield contour map), a X-ray image or a MRI image, attribute information such as name, date of birth, and distinction of sex of the subject, and data on the subject.

Further, computer processable software applicable to the magnetocardiograph, comprises: a step at which a heart magnetic signal measured is stored; a step at which a position of center of gravity of excitement wave front in a cardiac muscle excitement propagation process and a transition vector (hereinafter, referred to as a wave front vector) are calculated from the information of the heart magnetic signal stored; and a step at which an analysis result is displayed.

Also, a computer-readable storage medium stores the software in order to read-process by operating the computer.

Since it is possible to presume, from the measured data, whether or not the subject has a heart disease, and to quantitatively presume candidature for a factor of the heart disease, the present invention has an effect of being able to support the doctor's diagnosis. Also, since simple and easy analysis operation leads to the shortened diagnosis time period including the data analysis time period and also leads to prevention of a disease from being overlooked as compared with the technique of presuming from enormous data, this is effective for a group examination and the like.

DETAILED DESCRIPTION OF THE PREFERRED EMBODIMENTS

Figure 1:
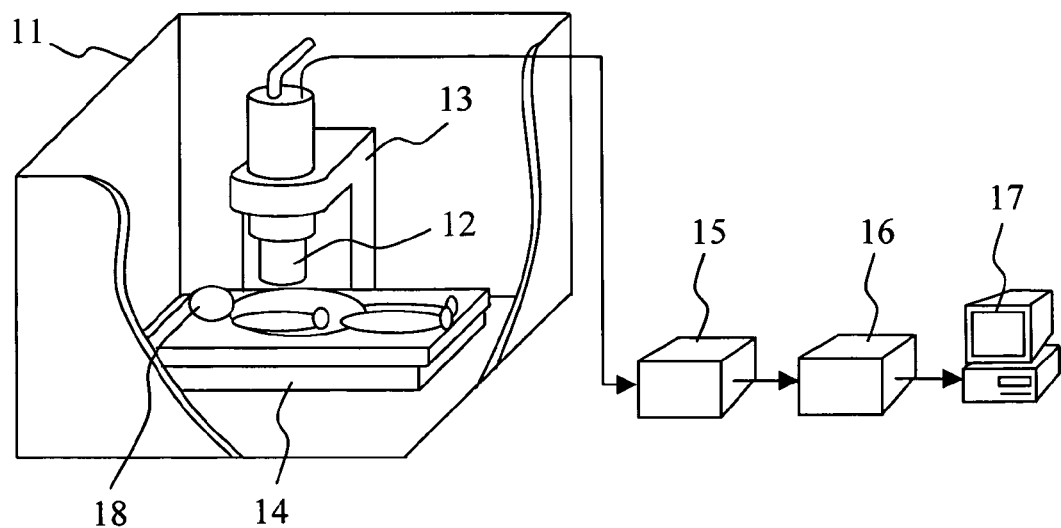
FIG. 1 is a block diagram showing a magnetocardiograph according to an example of the present invention.

With reference to the drawings, the description will be made of an embodiment of the present invention. FIG. 1 is a schematic block diagram showing an example of application of a magnetocardiograph according to the present invention. Within a magnetic shield room 11, there are arranged a bed 14 on which a subject 18 lies down, a plurality (plural channels) of SQUID magnetic sensors and a cryostat 12 in which refrigerant (liquid helium or liquid nitrogen) for holding the SQUID magnetic sensors in a superconductive state has been stored. The cryostat 12 is mechanically held by a gantry 13. The bed 14 is capable of ascending and descending, and moving in front and in rear, and left and right. In the outside of the magnetic shield room 11, there are arranged a SQUID fluxmeter operating circuit 15, an amplifier circuit and a filter circuit unit 16, and an analyzing computer 17 for taking in data for analyzing.

An organism magnetic signal detected by the SQUID magnetic sensor is amplified by the amplifier circuit and filter circuit unit 16. And after subjected to signal processing such as a low-pass filter through which a frequency signal lower than a preset frequency is passed, a high-pass filter through which a frequency signal higher than a preset frequency is passed, and a notch filter which cuts only commercial power source frequency, the organism magnetic signal is taken into the analyzing computer (personal computer) 17 as raw data. The analyzing computer 17 is capable of storing the raw data taken in a raw data file, screen-displaying waveform, analysis-processing waveform and also displaying the result. The analyzing computer 17 corresponds to calculation means, storage means and display means according to the present invention, and realizes each function to be described below by the software. In this respect, an object of the present invention is also computer-processable software and a storage medium for storing the software.

Figure 2:
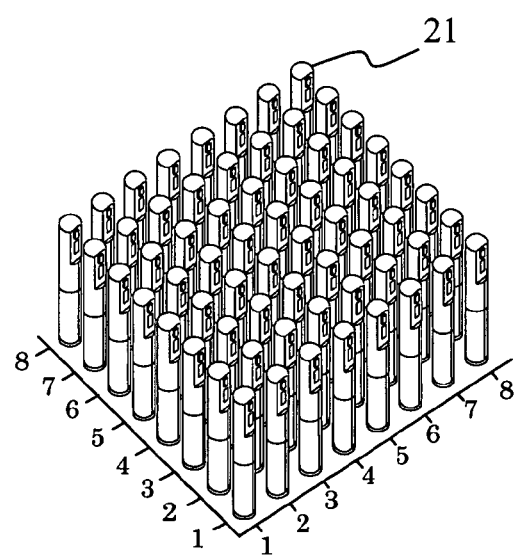
FIG. 2 is a schematic external appearance structural view showing a SQUID magnetic sensor in the magnetocardiograph.
Figure 3:
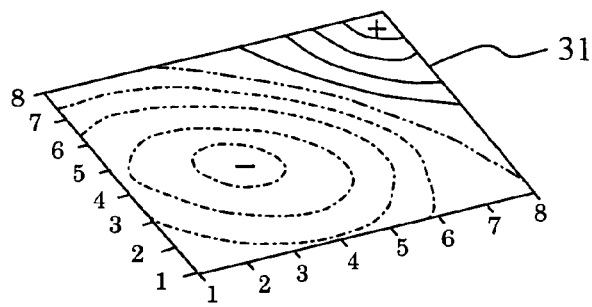
FIG. 3 is an isofield contour map (MCG map) showing a heart magnetic field obtained by detecting by the SQUID magnetic sensor.

FIG. 2 is a view showing an outline of external appearance structure and layout of the SQUID magnetic sensor. The SQUID magnetic sensor which has been kept cool within the cryostat 12 in FIG. 1 has a plurality of SQUID magnetic sensors arranged in space. Although in the example of FIG. 2, a total 64 pieces of 8×8 have been arranged, a number of the magnetic sensors may be optional. The plurality of SQUID magnetic sensors are arranged in space as described above, whereby such a MCG map 31 as shown in FIG. 3 can be prepared from output of the heart magnetism signal detected. The MCG map 31 is an isofield contour map of the heart magnetic field.

Heart magnetism measurement is to measure an external magnetic field generated by an electric current flowing when excitation-conduction neurocyte, cardiac muscle cell or the like of the heart gets excited. An action current which propagates within the cardiac muscle cell can be considered to be an intracellular ionic current. The excitement of the cardiac muscle cell travels as an excitation wave, and can be electrically considered to be an electrical double layer in which current dipoles have gathered on an excitement propagation wave front (tip of the excitement propagation). Therefore, a magnetic field generating source (electric current source) to be caught by the heart magnetism measurement can be considered to be only a boundary portion of the electrical double layer which is a tip portion (excitement wave front) to which the cardiac muscle cell gets excited and propagates. In other words, the magnetic field distribution which the excitement wave front causes in the cardiac muscle excitement propagation process is regarded as the MCG map.

In the present invention, in order to make into a parameter extracted as a feature in the analysis of the above-described excitement wave front, we have formed a concept of wave front vector. The wave front vector is represented by the position of center of gravity (X, Y coordinates on the MCG map) of excitement wave front and the transition vector (angle $\theta[rad]$).

Figure 4:
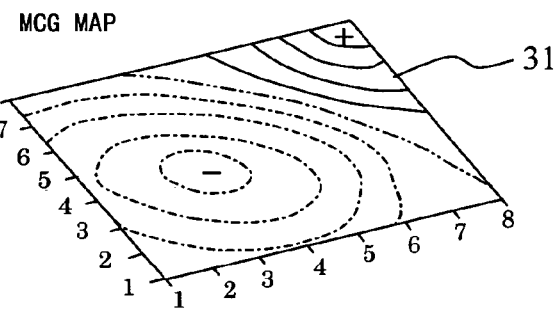
FIG. 4 is an explanatory view showing a wave front vector due to analysis of the present invention and a vector arrow map due to conventional analysis.
Figure 4:
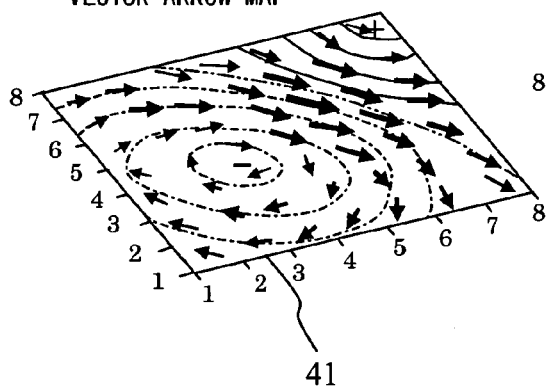
Figure 4:
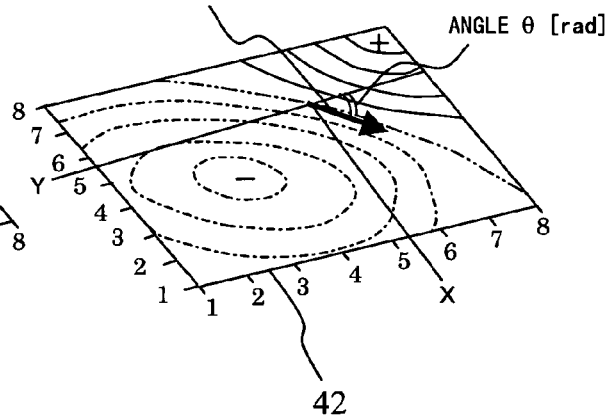

FIG. 4 is a view for explaining a wave front vector by an analysis of the present invention and a vector arrow map by a conventional analysis. The vector arrow map has been described in detail in "Organism Magnetic Measurement" (by Kotani and Uchikawa et al, 1995; published by Corona, Inc.) and the like. To briefly explain here, the vector arrow map 41 approximately determines distributed potential from the MCG map, and displays its direction and amplitude as a direction and amplitude of the arrow. Conventionally, they have judged a heart disease by viewing a difference in pattern of this vector arrow map.

In the wave front vector 42 according to the present invention, a wave front vector (X, Y, θ) is determined from the MCG map, and this wave front vector is analyzed as a feature parameter.

Figure 5:
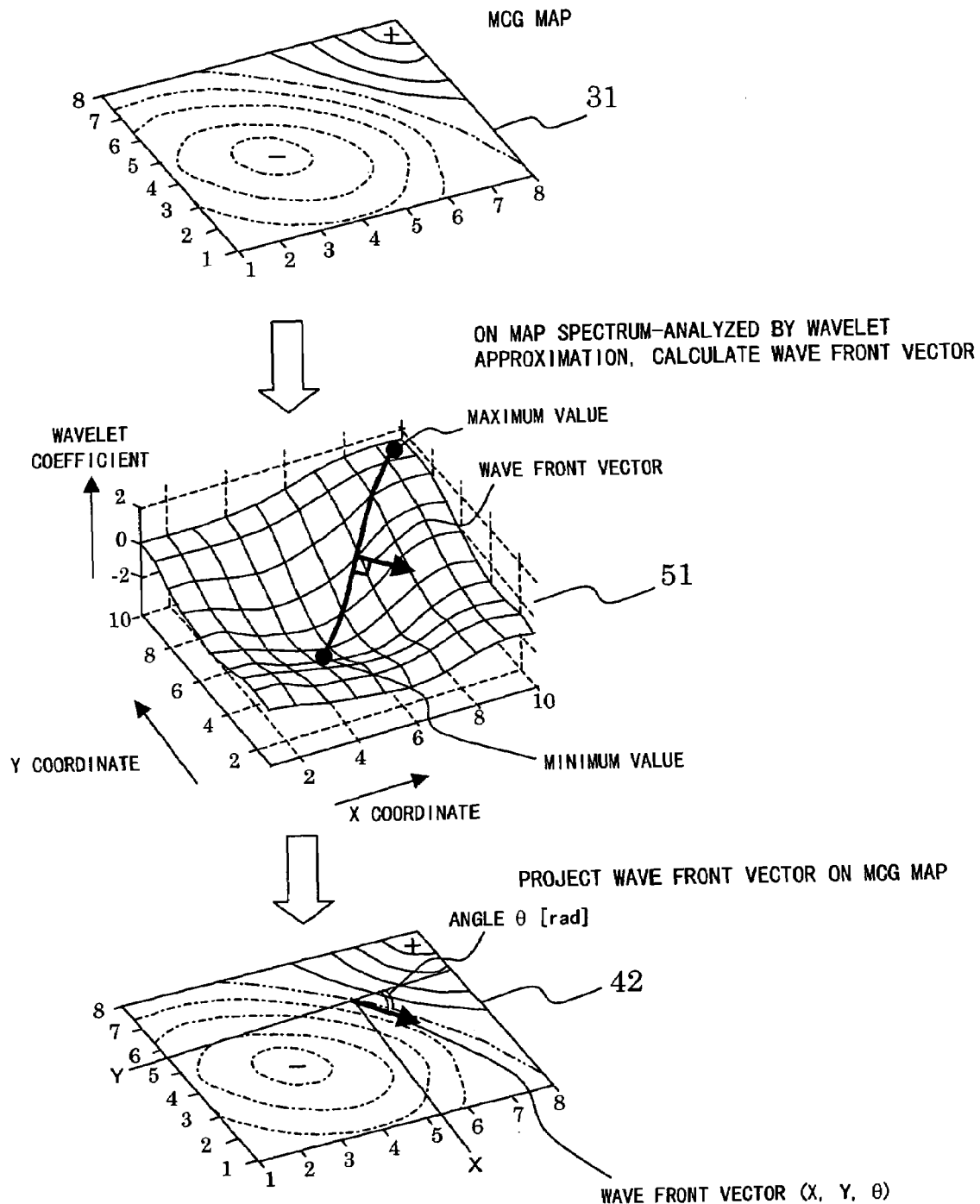
FIG. 5 is an explanatory view showing a process of calculation for determining a wave front vector from the MCG map.

FIG. 5 is a view for explaining a process of calculation for determining a wave front vector from the MCG map. From the MCG map 31, the wave front vector, that is, the position of center of gravity of excitement wave front and the transition vector in the cardiac muscle excitement propagation process will be calculated. The position of center of gravity of excitement wave front is located at the middle point between two magnetic field peaks of source and sink in the MCG map, and an advance direction (transition vector) of the excitement wave front is equal to a direction of an ionic current on the wave front. In other words, the advance direction is a direction of turning a right-handed screw from the magnetic field peak of source to the magnetic field peak of sink and is perpendicular to a line connecting the magnetic field peaks together. In this case, in order to improve the detection precision of the excitement wave front, using a technique of Wavelet approximation, which is a well-known technique in general spatial frequency analysis, the middle point between source and sink magnetic field peaks (maximum value and minimum value of Wavelet coefficient) on a spectrum-analyzed map 51 is regarded as the center of gravity.

Since for the general spatial frequency, there are also Fourier transform and Wavelet transform, these may be used in place of the Wavelet approximation. A view obtained by projecting a wave front vector determined by a map 51 by Wavelet approximation on the MCG map, and representing the wave front vector by X, Y coordinate and angle θ is a map 42 obtained by projecting the wave front vector.

In this respect, when source or sink magnetic field peak is not included within a range of the MCG map measured, extrapolation can be performed.

Figure 6:
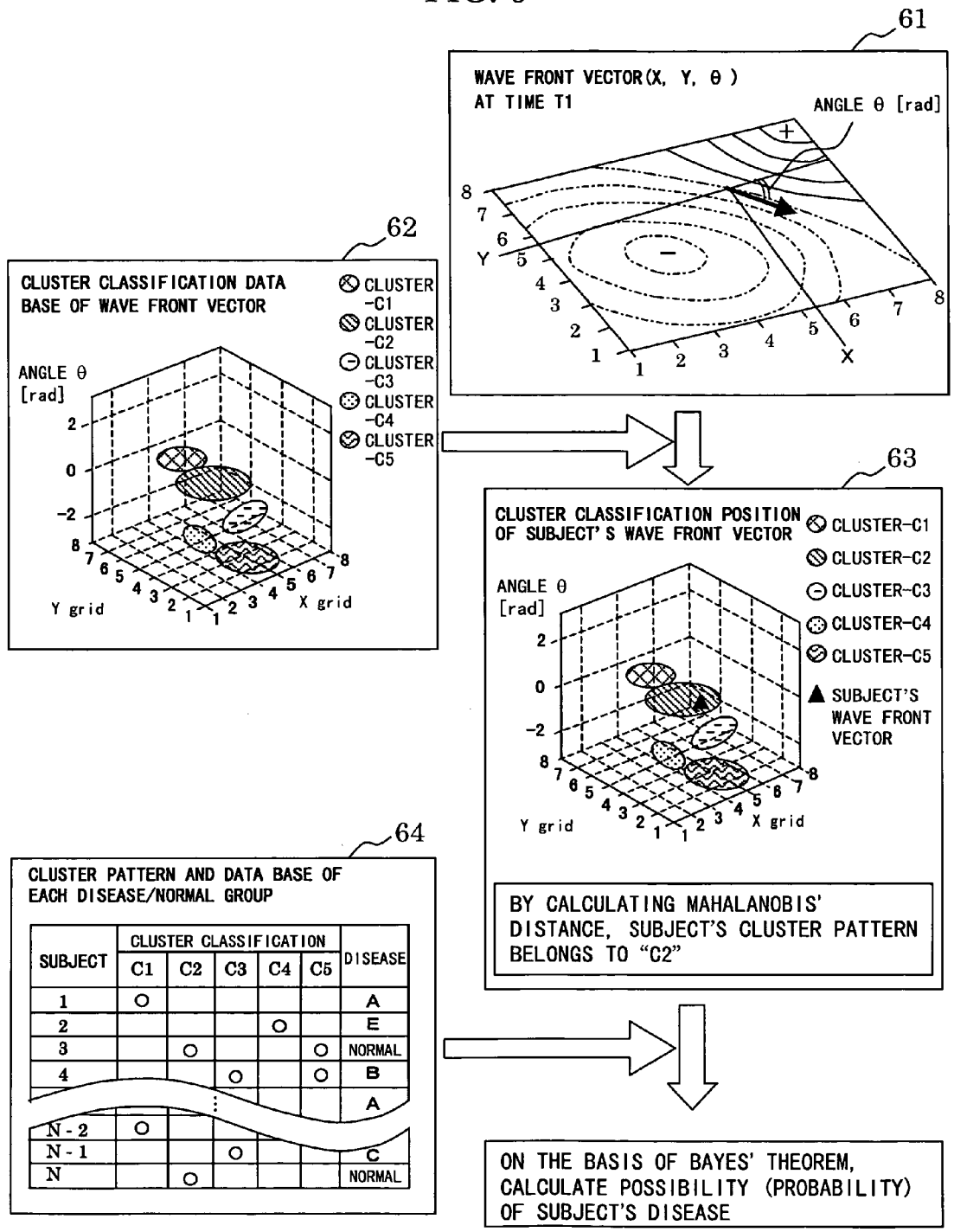
FIG. 6 is an explanatory view showing a process of calculating a possibility (probability) of a subject's disease with the wave front vector as a feature parameter.

FIG. 6 is a view for explaining a process of calculating possibility (probability) of the subject having a disease with the wave front vector as a feature parameter. Feature parameters (wave front vectors) obtained by measuring a plurality of subjects in advance are classified into several clusters as set of Gaussian distribution and is made into a data base 62 in advance. Next, it will be calculated in which cluster pattern in the data base 62 the subject's wave front vector 61 will be classified (63).

As means for calculating to which cluster pattern it belongs, a Mahalanobis' distance between the center of gravity of each cluster pattern and the wave front vector of the subject which should be classified will be calculated, and a cluster pattern which has been an extremely short distance will be regarded as the subject's cluster pattern. The Mahalanobis' distance has been described in detail in Document such as "Quality Engineering for Technical Development" by The Japan Standard Association.

A Mahalanobis' distance Dt between position Mt of center of gravity of a cluster Ct and the subject's wave front vector x is represented by Numerical Formula 1.

$$d_t(x) = \sqrt{(x - m_t)^T \sum_t^{-1} (x - m_t)}$$

where $$\sum_t^{-1}$$

represents an inverse matrix of the covariance matrix for the cluster Ct.

In FIG. 6, one wave front vector at time T1 is analyzed. However, there are cases where it is classified into a plurality of cluster patterns such as when there are multiple wave front vectors in one MCG map, and when wave front vectors of a plurality of MCG maps are analyzed as time series. In this case, a cluster pattern, to which extremely many wave front vectors have belonged, may be regarded as the subject's cluster pattern, or two cluster patterns, most of which has belonged to a first one and a second one, may be regarded as the subject's cluster pattern. Since there may be also cases where it becomes a feature to have a plurality of cluster patterns of wave front vector depending upon the disease, it is not limited in the present invention what number cluster pattern should be used.

Next, a possibility (probability) to what extent the subject's cluster pattern judged as described above applies to what heart disease will be calculated. In other words, using cluster classification of respective feature parameters (wave front vectors) obtained by measuring a plurality of previous subjects in advance, and a data base 64 obtained by collecting names of disease or normal persons already diagnosed, a possibility (probability) to what extent the subject's cluster pattern judged as described above applies to what heart disease will be calculated.

Hereinafter, the description will be made of the Bayes' theorem to be used in this calculation. The Bayes' theorem has been described in detail in Document such as "Bayers T, An essay towards solving a problem in the doctrine of chances. "Philosophical transactions (1763)" and "Introduction To Statistics by Nakamura, published by Tokyo University (1990)".

The Bayes' theorem shown in Numerical Formula 2 represents conditioned probability P{Si|Ck}, in which when it turned out that there are Ck (here, k=1, 2, 3, . . . , m) of parameters of a certain data, the data is included in a group Si (here, i=1, 2, 3, . . . , n).

$$P\{Si|Ck\} = \frac{P\{Si\}P\{Ck|Si\}}{\sum_{j=1}^{n} P(Sj)P(Ck|Sj)}$$

In the case of the present invention, Si designates heart disease groups which should be classified, and Ck, a cluster pattern to be obtained from the MCG map. A conditional probability P{Ck|Si} of the right side shows a probability that the cluster pattern is Ck when it is known that a certain subject belongs to a group of a disease Si. On the basis of these prior probabilities P{Si} and P{Ck|Si}, a posterior probability P{Si|Ck} can be determined. In other words, from cluster patterns of MCG data of a preliminary normal person and a heart disease patient and the diagnosis result, a possibility (probability) of each disease corresponding to each cluster pattern Ck can be calculated.

The description will be made using specific numerical values. It is assumed that a ratio of a normal group $S_1$ is 50% of the whole, that of a disease group $S_2$ is 20%, and that of a disease group $S_3$ is 30%, and that within the normal group $S_1$, a ratio of a cluster pattern $C_1$ is 80%, within the disease group $S_2$, a ratio of the cluster pattern $C_1$ is 20%, and within the disease group $S_3$, the ratio of the cluster pattern $C_1$ is 10%. Now, when the cluster pattern of a certain subject is $C_1$, the respective possibility (probability) of the normal group $S_1$, the disease group $S_2$ and $S_3$ is calculated as below.

Possibility of being normal group $S_1$:

$$P\{S_1|C_1\}=0.5\times0.8/(0.5\times0.8+0.2\times0.2+0.3\times0.1)=0.851$$
$$(=85.1\%)$$

Possibility of being disease group $S_2$:

$$P\{S_2|C_2\}=0.2\times0.2/(0.5\times0.8+0.2\times0.2+0.3\times0.1)=0.085$$
$$(=8.5\%)$$

Possibility of being disease group $S_3$:

$$P\{S_3|C_3\}=0.3\times0.1/(0.5\times0.8+0.2\times0.2+0.3\times0.1)=0.064$$
$$(=6.4\%)$$

As display means for possibility (probability) of each disease, merely numerical percentage display may be used, and a visual graph display may be also used. By displaying probability of to what extent it is a normal person and probability of to what extent it applies to what heart disease, it will aid when the doctor is diagnosing a heart disease, and finally, the doctor will diagnose with all things including other examinations considered.

Figure 7:
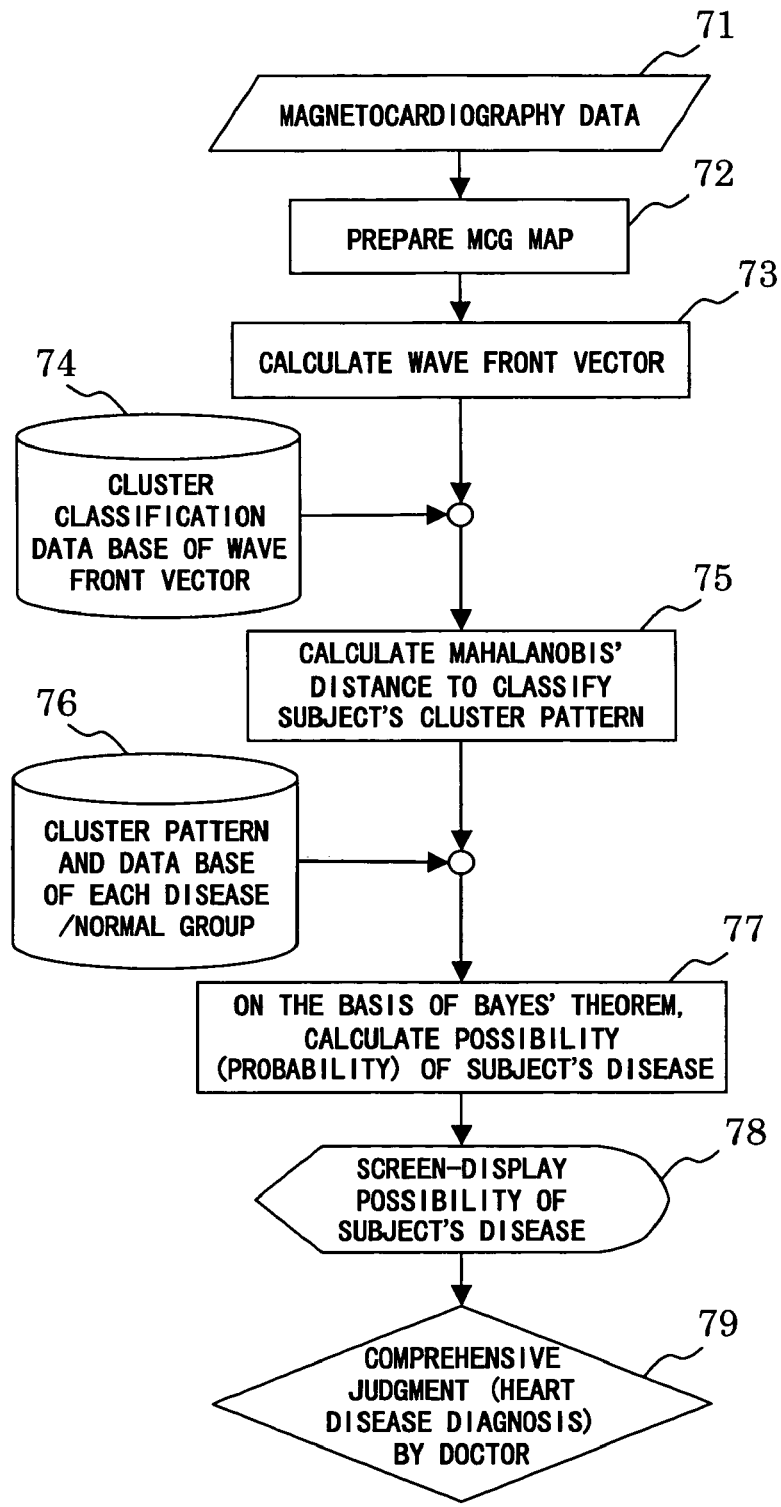
FIG. 7 is a processing flow diagram showing a procedure for determining a wave front vector by an analyzing computer according to an example of the present invention and calculating a possibility (probability) of a disease.

FIG. 7 is a processing flow diagram by an analyzing computer according to the present example. A data analyzing computer 17 first prepares a MCG map from heart magnetism measurement data 71 received from the magnetic sensor (72). Next, the wave front vector will be calculated from the MCG map (73). The detail of calculation of the wave front vector is as explained in FIG. 5.

Next, from the subject's wave front vector calculated and the cluster classification data base 74 of the wave front vector, the Mahalanobis' distance will be calculated to classify the subject's cluster patterns (75). Next, from the cluster pattern and the data base 76 of each disease/normal groups, the possibility (probability) of disease of the subject will be calculated on the basis of the Bayes' theorem (77) to display on the screen (78). The detail of calculation 78 of possibility (probability) of the subject's disease from the cluster classification data base 74 of the wave front vector on the basis of the Bayes' theorem is as explained in FIG. 6. Finally the doctor will comprehensively judge by seeing a calculation result of possibility (probability) of the subject's disease by the above-described processing flow for heart disease diagnosis (79).

Figure 8:
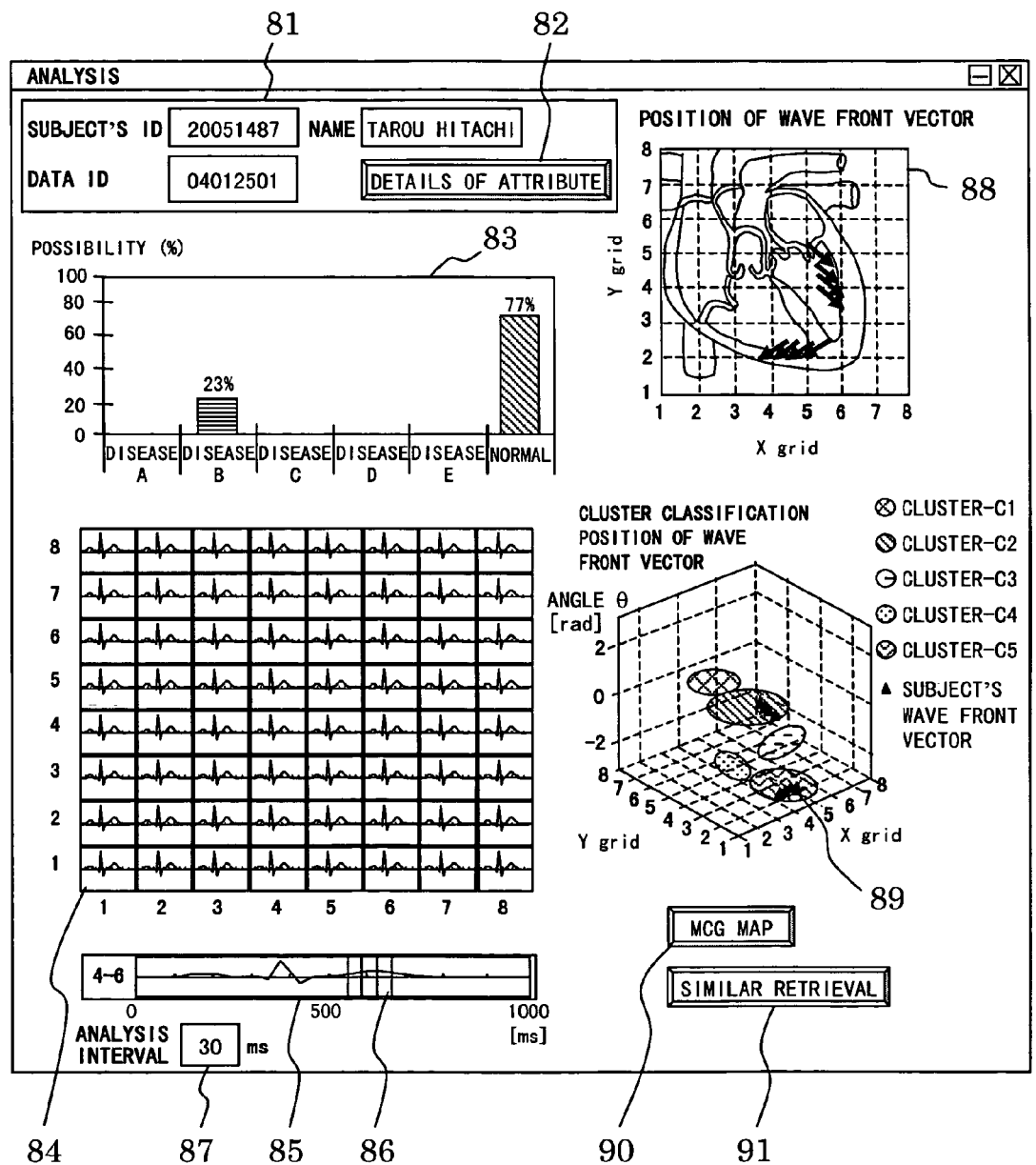
FIG. 8 is an explanatory view showing a view display of heart magnetism measurement according to an example of the present invention.
Figures 9, 10:
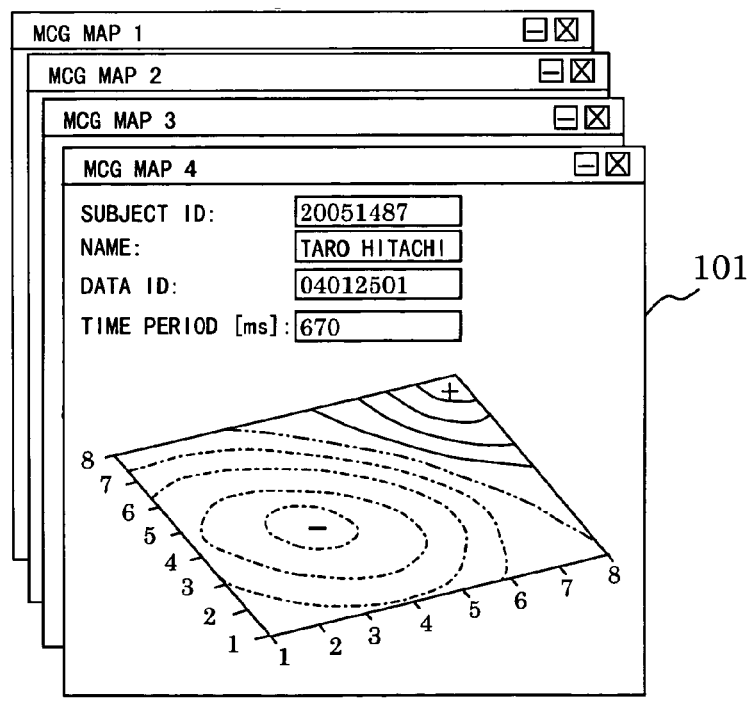
FIG. 9 is an explanatory view showing detailed attribute display window of the subject.
FIG. 10 is an explanatory view showing a MCG map display window of the subject.

FIG. 8 shows a screen display example according to the present example. In an input box 81 of an analyzing screen window, ID of a subject which should be analyzed and data ID will be inputted. When the subject ID is inputted, the name will be displayed. Further, when an attribute detailed display button 82 is clicked, the subject attribute detailed display window 95 of FIG. 9 is displayed, and detailed attribute information such as the date of birth, height and weight of the subject can be confirmed.

The window 83 of FIG. 8 is a calculation result display area (graph display) of the possibility (probability) of the subject's disease. A window 84 is a waveform display area of a heart magnetic signal measured. Here, in accordance with arrangement of each sensor channel, a magnetic field-time waveform obtained by measuring with each sensor channel is displayed on the matrix.

When the sensor channel is designated on the matrix of the window 84, a magnetic field-time waveform is displayed on the window 85. For example, in this figure, a sensor channel at line 4 and column 6 (4-6) is displayed. In the magnetic field-time waveform of the window 85, a time interval 86 which should be analyzed will be set. In a time interval 86, the MCG map every what ms is analyzed is inputted into an analysis interval 87. For example, when the time interval 86 is set from 580 ms to 670 ms and the interval 87 is set to 30 ms, the MCG map in 580 ms, 610 ms, 640 ms and 670 ms will be analyzed.

A position of the wave front vector analyzed is displayed on the window 88. In order to make a position of the wave front vector easier to understand, the window 88 superimposes on a heart picture prepared in advance for displaying. Also, an X-ray CT image of the subject prepared in advance or the MRI image may be used.

The window 89 is obtained by displaying a cluster classification position of the subject's wave front vector in three dimensions. Thereby, the subject's cluster pattern can be confirmed in a visual form.

When a MCG map display button 90 is clicked, a MCG map display window 101 of FIG. 10 is displayed. Thereby, the subject's MCG map can be confirmed.

When a similar retrieval button 91 is clicked, the subject's feature parameter (wave front vector) and a feature parameter of another subject having a minimum Mahalanobis' distance, that is, extremely similar will be retrieved from the data base, whereby the subject's data will be able to be called.

Figure 11:
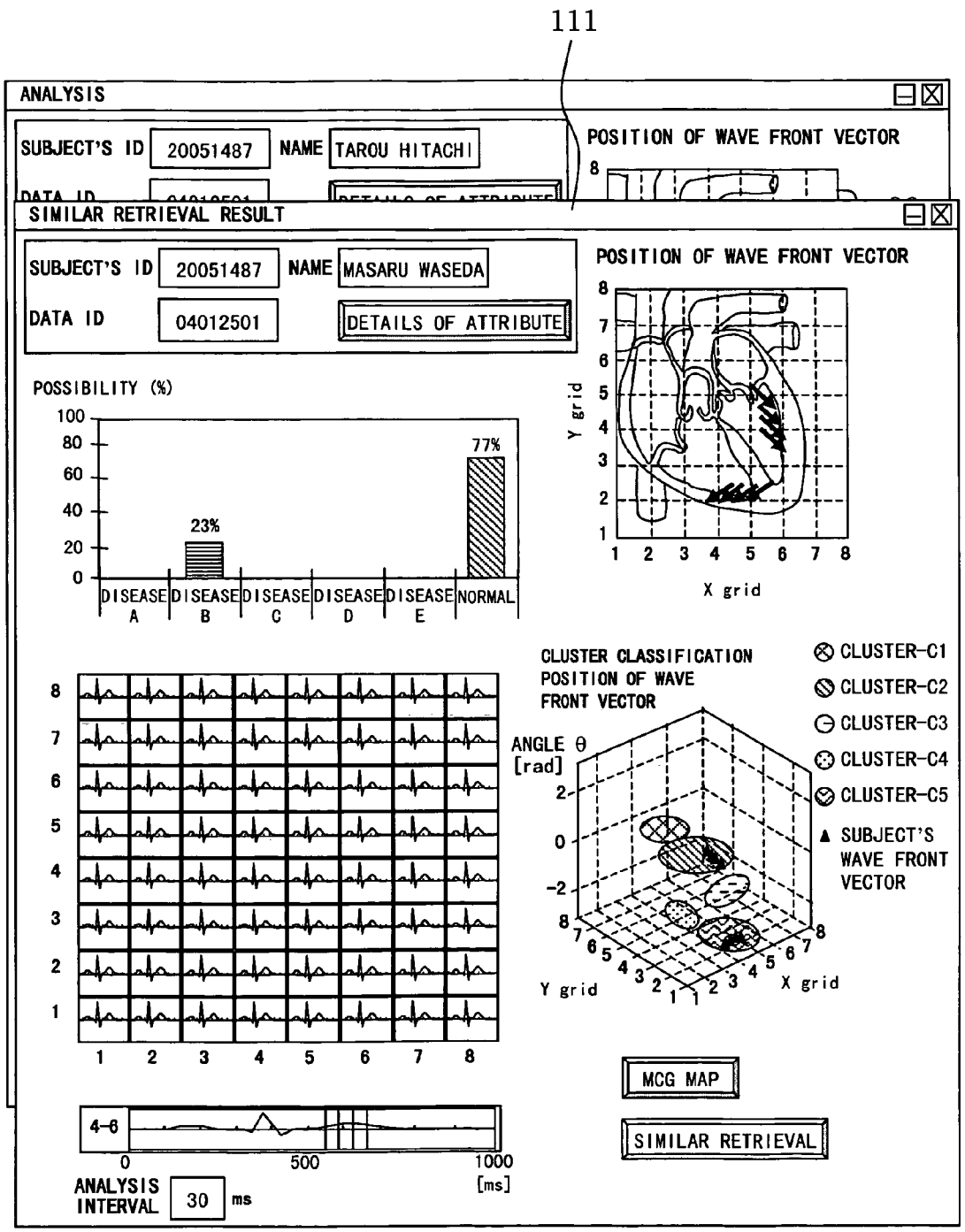
FIG. 11 is an explanatory view showing a similar retrieval result display window to be displayed by similar retrieval.

FIG. 11 is an example of screen display of a similar retrieval result. This screen displays a retrieval result of another subject Masaru Waseda 111 extremely similar to a subject Taro Hitachi 81.

According to the present example, since whether or not the subject has a heart disease, and candidature of a factor of heart disease can be quantitatively presumed, it is capable of supporting a doctor's diagnosis without relying on subjective experience and judgment of the doctor. And since the analysis operation is simple and easy, the diagnosis time period including the data analysis time period can be shortened. Also, as compared with a technique of presuming from enormous data, it is also possible to prevent a disease from being overlooked.

What is claimed is:

1. A magnetocardiograph for measuring magnetism to be generated from a subject's heart by at least one magnetic sensor comprising:

storage means for storing a heart magnetic signal thus measured;

calculation means for calculating a position of center of gravity of excitement wave front in a cardiac muscle excitement propagation process and a transition vector (hereinafter, referred to as a wave front vector) from information of the heart magnetic signal stored in said storage means; and display means for displaying an analysis result, wherein said calculation means prepares an isofield contour map for a heart magnetic field from said heart magnetic signal, calculates said wave front vector on the isofield contour map obtained by spectrum analyzing by means of Wavelet approximation, and projects the calculated wave front vector on the isofield contour map before the Wavelet approximation.

2. The magnetocardiograph according to claim 1, wherein said calculation means regards said wave front vector as a feature parameter, and classifies cluster patterns of said previous subjects based on a cluster classification data base of feature parameters obtained by measuring a plurality of previous subjects in advance.

3. The magnetocardiograph according to claim 2, wherein said calculation means calculates a Mahalanobis' distance between a center of gravity of each cluster pattern of said cluster classification data base and the feature parameter of said subject, and judges to which cluster pattern the feature parameter of said subject belongs based on the information of the Mahalanobis' distance obtained.

4. The magnetocardiograph according to claim 3, wherein said calculation means calculates probability of being a normal person and probability of being a disease patient from the judgment result using said cluster pattern.

5. The magnetocardiograph according to claim 4, wherein said calculation means determines said probability on the basis of Bayes' theorem.

6. The magnetocardiograph according to claim 4, wherein said calculation means judges whether the subject is a normal person or a heart disease patient based on said probability of being a normal person and probability of being a heart disease patient.

7. The magnetocardiograph according to claim 4, wherein said calculation means calculates at what probability various heart diseases are applied to the subject, for displaying.

8. The magnetocardiograph according to claim 3, wherein said calculation means retrieves data of another subject extremely close (similar) to the Mahalanobis' distance determined concerning said subject from said cluster classification data base.

9. The magnetocardiograph according to claim 2, wherein said calculation means displays a feature parameter of said subject classified on said cluster pattern.

10. A magnetocardiograph for measuring magnetism to be generated from a subject's heart by at least one magnetic sensor comprising:
    storage means for storing a heart magnetic signal thus measured;
    calculation means for calculating a position of center of gravity of excitement wave front in a cardiac muscle excitement propagation process and a transition vector (hereinafter, referred to as a wave front vector) from information of the heart magnetic signal stored in said storage means; and
    display means for displaying an analysis result, wherein said calculation means prepares an isofield contour map for a heart magnetic field from said heart magnetic signal, calculates said wave front vector on the isofield contour map, and projects the calculated wave front vector on the isofield contour map.

11. A magnetocardiograph for measuring magnetism to be generated from a subject's heart by at least one magnetic sensor comprising:
    storage means for storing a heart magnetic signal thus measured;
    calculation means for calculating a position of center of gravity of excitement wave front in a cardiac muscle excitement propagation process and a transition vector (hereinafter, referred to as a wave front vector) from information of the heart magnetic signal stored in said storage means; and
    display means for displaying an analysis result, wherein said calculation means prepares an isofield contour map for a heart magnetic field from said heart magnetic signal, calculates said wave front vector on the isofield contour map obtained by spectrum analyzing by means of Fourier transformation, and projects the calculated wave front vector on the isofield contour map before the Fourier transformation.

12. A magnetocardiograph for measuring magnetism to be generated from a subject's heart by at least one magnetic sensor comprising:
    storage means for storing a heart magnetic signal thus measured;
    calculation means for calculating a position of center of gravity of excitement wave front in a cardiac muscle excitement propagation process and a transition vector (hereinafter, referred to as a wave front vector) from information of the heart magnetic signal stored in said storage means; and
    display means for displaying an analysis result, wherein said calculation means prepares an isofield contour map for a heart magnetic field from said heart magnetic signal, calculates said wave front vector on the isofield contour map obtained by spectrum analyzing by means of Wavelet transformation, and projects the calculated wave front vector on the isofield contour map before the Wavelet transformation.

* * * * *